(12) United States Patent
Mitchell

(10) Patent No.: US 7,686,794 B2
(45) Date of Patent: Mar. 30, 2010

(54) FEMININE HYGIENE SHORT

(76) Inventor: Diane M. Mitchell, 14 Merrick Rd., Poughkeepsie, NY (US) 12603

(\*) Notice: Subject to any disclaimer, the term of this patent is extended or adjusted under 35 U.S.C. 154(b) by 1472 days.

(21) Appl. No.: 10/245,350

(22) Filed: Sep. 17, 2002

(65) Prior Publication Data
US 2004/0054340 A1 Mar. 18, 2004

(51) Int. Cl.
*A61F 13/15* (2006.01)
(52) U.S. Cl. .............. 604/385.25; 604/385.3; 604/396; 2/78.3; 2/401
(58) Field of Classification Search ................ 604/385.24–385.25, 385.3, 393–396; 2/78.1–78.3, 2/401, 407
See application file for complete search history.

(56) References Cited

U.S. PATENT DOCUMENTS

| | | | | |
|---|---|---|---|---|
| 3,508,550 A | * | 4/1970 | Vollrath | 604/394 |
| 3,714,946 A | * | 2/1973 | Rudes | 604/394 |
| 4,555,245 A | * | 11/1985 | Armbruster | 604/396 |
| 4,813,950 A | * | 3/1989 | Branch | 604/396 |
| 4,880,424 A | * | 11/1989 | Rautenberg | 604/396 |
| 5,921,974 A | * | 7/1999 | Kikuchi | 604/385.24 |
| 5,944,708 A | * | 8/1999 | Philpott | 604/393 |
| 6,120,489 A | * | 9/2000 | Johnson et al. | 604/386 |
| 6,626,883 B2 | * | 9/2003 | Wada et al. | 604/396 |

\* cited by examiner

*Primary Examiner*—Tatyana Zalukaeva
*Assistant Examiner*—Lynne Anderson
(74) *Attorney, Agent, or Firm*—Joseph B. Taphorn

(57) ABSTRACT

A feminine hygiene device offers full protection from heavy menstrual flow by securely covering the inner thigh, buttocks and pelvic area against menstrual leakage. The hygiene device is in the nature of a pair of shorts having vertical elastic seams on each side to hold the device snug on the wearer's pelvic region and legs. Elastic elements on the bottom of each leg of the short secure against downward leakage. The short is made of a liquid impervious cloth having an absorbent cotton blend layer and an outer plastic layer. Additional absorbent padding is incorporated in the short to provide normal coverage in the vaginal region. An elastic waist element aides in supporting the device on the wearer. The cloth may be vapor permeable and the side vertical seams air permeable for cooling effects. A diaper may be readily fashioned of the device.

20 Claims, 2 Drawing Sheets

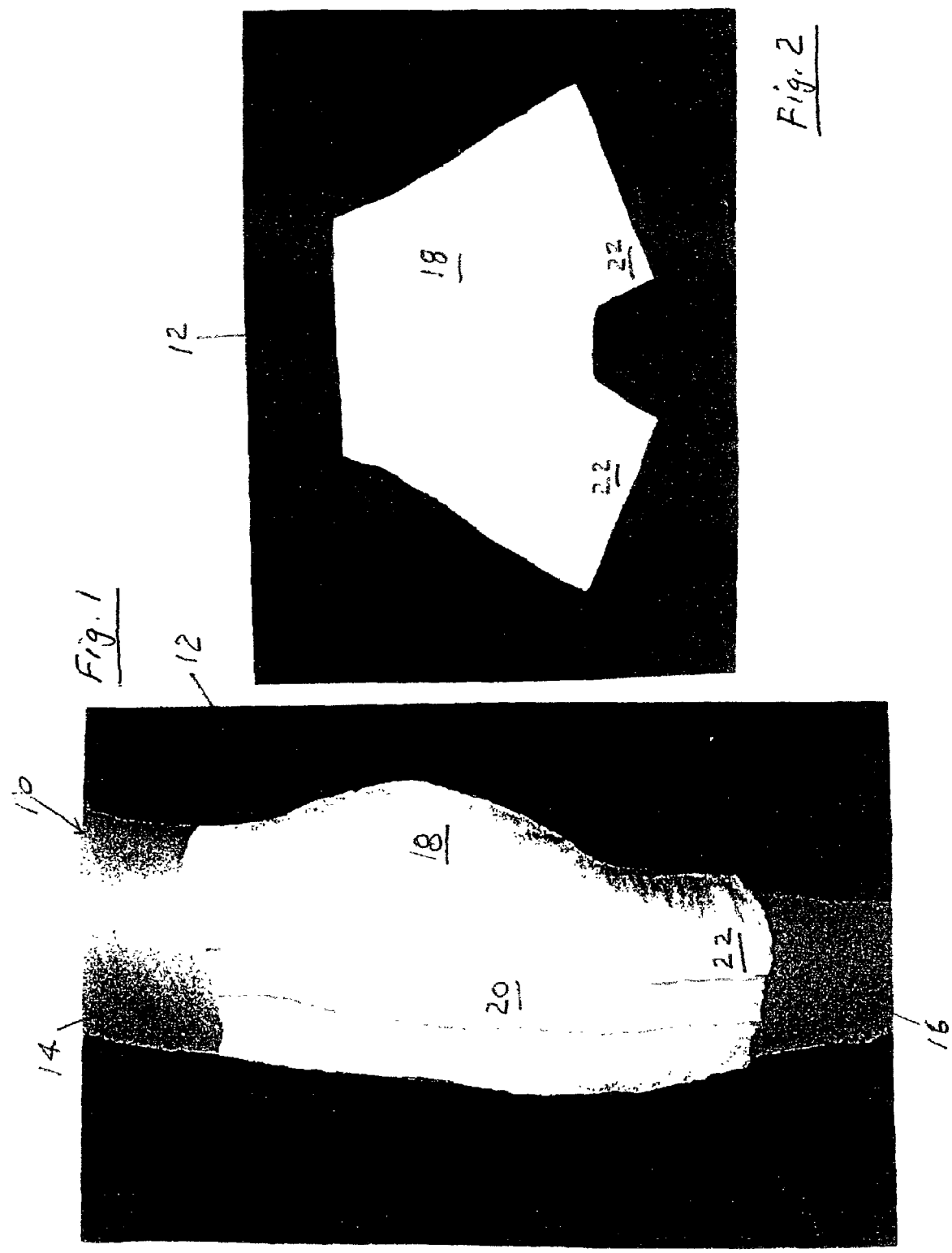

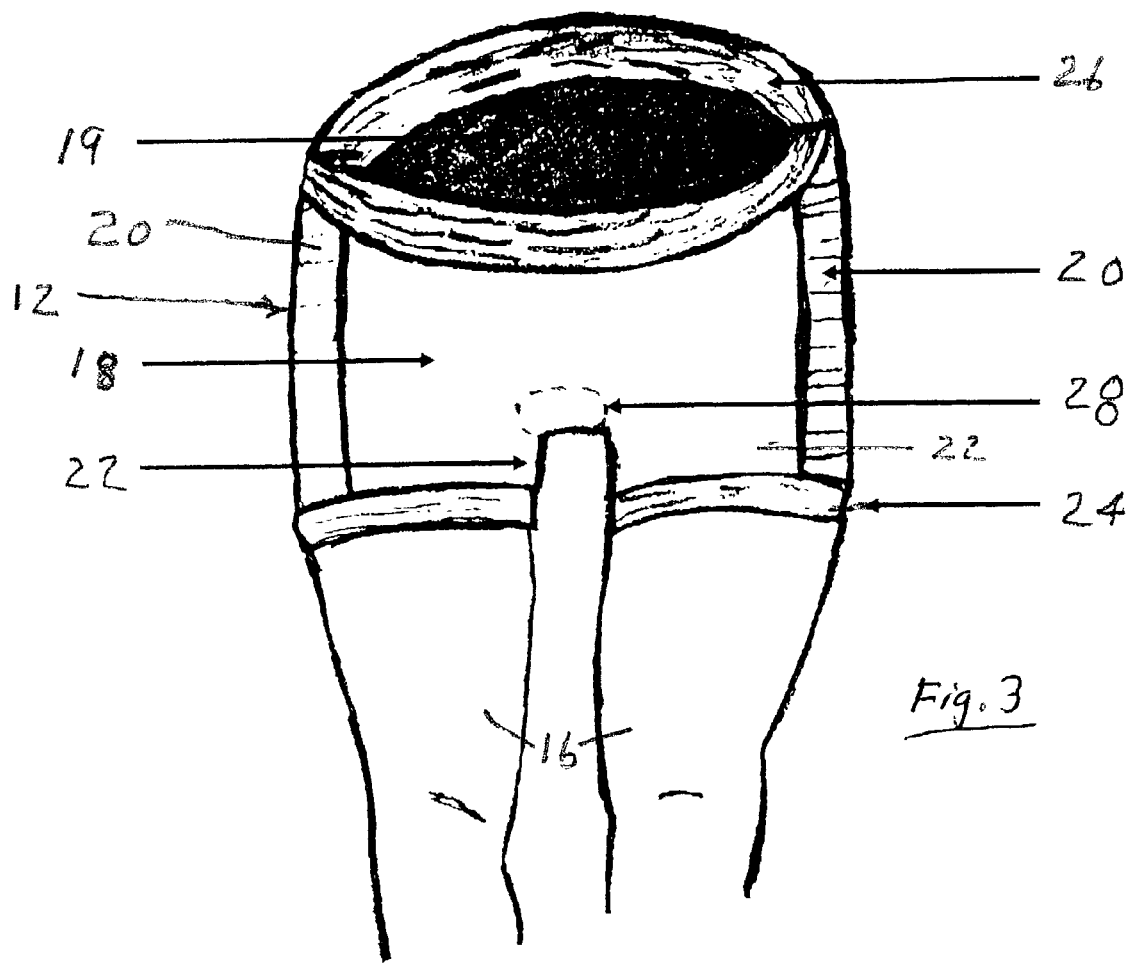
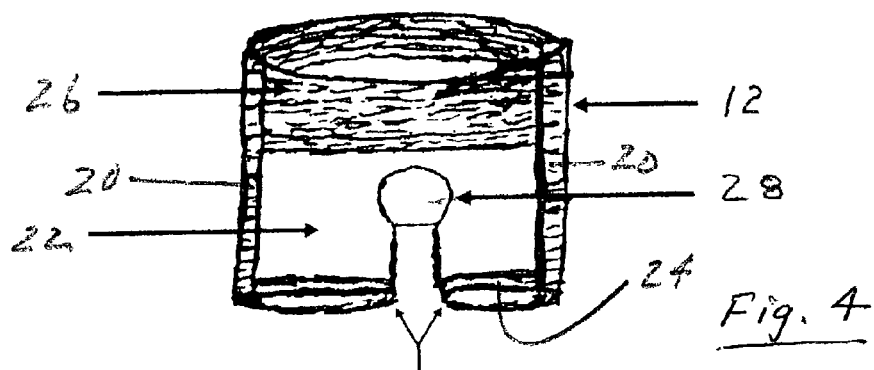
Fig. 3
Fig. 4

FEMININE HYGIENE SHORT

FIELD OF THE INVENTION

This invention relates to a feminine hygiene product for menstrual protection, and more particularly, to a feminine hygiene product offering full protection against heavy menstrual flow.

1. Background of the Invention

Menstruation recurs in non-pregnant breeding-age women at approximately monthly intervals. It involves the menstrual flow or menses, which is a discharge of blood, secretions, and tissue debris from the uterus via the vagina.

The monthly menstrual period is frequently colloquially referred to as that "time of the month". The monthly menstrual bleeding may require time-consuming and distressing, and sometimes embarrassing, cleaning of menses from clothing, bedding, furniture, etc.

2. Prior Art

Various products have been designed to handle menstrual flow. Included among these products are absorptive pads offering coverage in the vaginal region. Most women, particularly physically-active women, need more protection.

Diapers, of course, are well known. Hein U.S. Pat. No. 3,530,859 issued Sep. 29, 1970 discloses an infant's diaper having an absorbent inner layer and a less absorbent outer layer.

Daville U.S. Pat. No. 4,338,939 discloses incontinence pants worn by a person about the waist and narrowly about and between the legs having a supporting garment with front and back sides, retaining flaps affixed to the front and the back sides, an absorbent disposable diaper, and fasteners affixed to each pair of retaining flaps so human waste matter is retained by the diaper.

United Kingdom patent no. GB 2 167 304 A, discloses an adult incontinence device that is a three-layer unit used in connection with a sponge. The unit's perforated top layer passes urine to a one-way valve intermediate layer whose flap valves depress into aligned holes in a lower layer below which resides the sponge.

Women do not like wearing diapers. Beside being bulky, and adding unwanted dimension to the derriere and thus being silhouette disturbing, they can be downright uncomfortable.

SUMMARY OF THE INVENTION

Accordingly it is an object of the invention to provide a feminine hygiene product offering more protection against menstrual flow.

It is another object of the invention to eliminate time-consuming and distressing cleaning of menses from clothing, bedding, furniture, etc.

Still another object of the invention is to provide a feminine hygiene product offering full protection against heavy menstrual flow.

Yet another object of the invention is to provide a feminine hygiene product that is less bulky than a diaper.

A further object of the invention is to provide a feminine hygiene product that does not add an unwanted dimension to the derriere and is thus not silhouette disturbing.

A still further object of the invention is to provide a feminine hygiene product that is comfortable to wear.

The objects of the invention are achieved by constructing a feminine hygiene device as a pair of shorts with elastic seams to hold the cloth of the shorts snug about the pelvic region and adjacent leg portion of the wearer. The cloth itself is a soft absorbent layer backed up by a liquid impervious material like plastic. The absorbent layer takes up any menstrual flow which escapes past a thicker interior padding, such as a normal absorbent pad, carried in the vaginal area by the shorts. An elastic seam or band about the end of each leg of the short, insures that no menstrual flow escapes down a leg of the wearer and that it is absorbed by the cloth absorbent layer. An elastic seam or band about the upper end of the short aides in supporting the device on the wearer.

The cloth liquid impervious material may be vapor permeable to facilitate the escape of heat. The elastic side seams may be quite open to the passage of air to facilitate the escape of heat.

A feature of the invention is that the feminine hygiene device can be worn anytime. Of course, it is a "must have" while visiting relatives or business associates where an accident on their bedding or furniture could prove quite awkward.

Another feature of the invention is that the feminine hygiene device is lightweight, disposable, and provides full coverage for day and night.

An advantage of the invention is that it renders the use of absorbent pads "fail safe". Some poorly made pads fall apart on occasions. With active woman, absorbent pads sometimes shift due to weak adhesive. With the instant invention, the pads are held in place and none of these accidents which end up in embarrassing results occurs.

Another advantage of the invention is that the feminine hygiene device is undetectable under dresses, skirts, and most other clothing.

Still another advantage of the invention is that the hygiene device can be readily adapted to be used as a baby diaper to avoid leakage onto the diaper-changer's clothing or onto the changing table.

BRIEF DESCRIPTION OF DRAWINGS OF PREFERRED EMBODIMENTS OF THE INVENTION

These and other objects, features, and advantages of the invention will become apparent from a reading of the following description of a preferred embodiment of the invention, when considered with the attached drawings wherein:

FIG. 1 is a view in perspective (photograph) of the middle of the left side of a women wearing the feminine hygiene device according to the invention;

FIG. 2 is a view in perspective (photograph) of the front of the feminine hygiene device of FIG. 1;

FIG. 3 is a diagrammatic front view of the feminine hygiene device according to the invention on the pelvic region and legs of a wearer; and FIG. 4 is a diagrammatic front view of the feminine hygiene device according to the invention having its top and its bottom portions slightly tipped forward.

DETAILED DESCRIPTION OF THE PREFERRED EMBODIMENTS OF THE INVENTION

Referring now to the drawings, there is shown in FIG. 1 the middle portion of a women generally indicated by the 10 wearing the feminine hygiene device according to the invention generally indicated by the numeral 12. The woman has a waist 14 and legs 16 and derriere (unnumbered) there between.

The hygiene device 12 encompasses the women's derriere (unnumbered) and is generally formed of a moisture-impervious cloth 18. This moisture-impervious cloth 18 may be constituted of layers of an absorbent cotton blend material 19 and a thin plastic backing to prevent leakage throughout the thigh, buttocks, and vaginal regions. An exterior layer of soft cotton blend material may obtain for purposes of appearance and feel.

The cloth 18 is disposed where menstrual flow may occur, and thus defines more or less the front and back halves of the device. On the sides of the device however, where menstrual flow is unlikely to appear, wide elastic side bands 20 are attached to the side edges of the front and back halves of the cloth 18, to hold the device and particularly the cloth 18 in snug relation, or stretch-fit, to the derriere or pelvic region of a wearer and to accommodate flexing of the contained body parts, and well as some differences in body parts sizes. The mating side edges of the cloth 18 are preferably separated by the associated elastic side bands 20 for temperature comfort purposes; however, the front and back halves of the cloth 18 may be integral, with the elastic side bands overlapping some of the material in a folded condition to accommodate expansion of the device.

At its lower end, the hygiene device is formed with two legs 22 (see FIG. 2) for superior menstrual protection, the two legs rendering the device in essence a pair of shorts. The two legs 22 cover the upper portions of the legs 16 of a women wearing the device, and too are constituted, for the most part, of the moisture impervious cloth. The legs 22 of the device 12 are held in snug relation to the legs 16 of the device wearer by extending the extending the elastic side bands 20 down to the lower ends of the device legs 22.

The lower ends of the legs 22 of the shorts 12 are preferably provided with elastic threading (FIGS. 1 and 2) that reduce their cloth circumferences beyond that dictated otherwise by the cloth measurements, so that they snugly embrace the woman's legs 16 to prevent leakage there past while being expandable to accommodate different-sized thighs. Elastic bands 24 (FIGS. 3 and 4) may be substituted for the elastic threading on the lower ends of the legs 22 to prevent leakage there past.

The upper end of the device too may incorporate elastic threading (FIGS. 1 and 2) to further reduce the circumference thereof for enabling the upper end to firmly embrace a women's waist 14 to assist in supporting the device 12 in place on the wearer's body. This allows the tension exerted by the elastic side bands to be less, offering more comfort and ease of movement to the device wearer. The elastic threading also insures that no menstrual leakage occurs at the upper end when the wearer is in the horizontal position as during sleep. The elastic threading may be replaced by an elastic band 26 (FIGS. 3 and 4) that extends around the waist.

A thicker interior padding 28 (FIGS. 3 and 4), such as a normal absorbent pad, is carried in the crotch of the shorts so as to be disposed in the vaginal area of the wearer.

When worn, the feminine hygiene device 12 absorbs menstrual flow primarily the absorptive pad. Flow missing or overflowing the pad will be absorbed by the absorbent layer of the cloth 18. Flow missing or overflowing the absorbent will be prevented from leaving the device by the elastic elements on the short legs and waist. Freedom of movement by the wearer will be accommodated by the side elastic seams.

As noted earlier, the hygiene device can be readily adapted to be used as a baby diaper to avoid leakage onto the diaper-changer's clothing or onto the changing table. For example, the connections between the front vertical edges of the side bands 20 and the vertical side edges of the front half of the cloth 18 may be like VELCRO ones. Thus with a baby lying on its back with a soiled diaper, the front half of the cloth 20 may be quickly detached from the bands 20 fixed to the rear half of the cloth 20 which remained under the baby, the baby's bottom wiped with a downward action of the front half which would then be rolled up under a raised baby bottom, and the entire device removed without any leakage past the legs. On mounting a new diaper on the baby, the back half would be placed under a raised baby bottom, the baby bottom lowered, the diaper front half moved to cover the baby's pelvic region, and the side bands 20 stretched to were their associated VELCRO connection portions could be placed on the cloth front half side edges associated VELCRO connection portions.

While applicants have shown and described a preferred embodiment of the invention, it will be apparent to those skilled in the art that other and different applications may be made of the principles of the invention. It is desired therefore to be limited only by the scope or spirit of the appended claims.

What is claimed is:

1. A feminine hygiene device comprising a liquid impervious cloth having separated front and back halves with side edges for covering the pelvic region and upper parts of the legs of a woman, and wide elastic side bands attached to the side edges of the cloth front and back halves for tensioning the cloth snugly about the pelvic region and the legs and accommodating expansion of the device.

2. A feminine hygiene device according to claim 1, and additional absorptive padding borne by the cloth so as to be disposed below the vaginal area of a woman wearing the device.

3. A feminine hygiene device according to claim 1, wherein the cloth is layers of absorbent cotton blend material and a thin plastic backing.

4. A feminine hygiene device according to claim 2, wherein the cloth is layers of absorbent cotton blend material and a thin plastic backing.

5. A feminine hygiene device according to claim 1, and an elastic element associated with the bottom of each of the cloth portions for covering the upper parts of the legs of a woman for sealingly engaging the corresponding leg against menstrual flow.

6. A feminine hygiene device according to claim 2, and an elastic associated with the bottom of each of the cloth portions for covering the upper parts of the legs of a woman for sealingly engaging the corresponding leg against menstrual flow.

7. A feminine hygiene device according to claim 6, wherein the cloth is layers of absorbent cotton blend material and a thin plastic backing.

8. A feminine hygiene device according to claim 2, and an elastic element associated with the upper end of the cloth for covering the woman's pelvic region for helping support the device on the woman.

9. A feminine hygiene device according to claim 5, and an elastic element associated with the upper end of the cloth for covering the woman's pelvic region for helping support the device on the woman, and the cloth is vapor permeable and the elastic side bands air permeable.

10. A feminine hygiene device according to claim 9, and additional absorptive padding borne by the cloth so as to be disposed below the vaginal area of a woman wearing the device.

11. A hygiene device in the nature of a short, comprising a liquid impermeable cloth having separated front and back halves with side edges for partially encircling the pelvic region and adjacent leg portions of a person, and a wide elastic side band attached to the side edges of the cloth front and back halves for completing the encircling of the cloth about the pelvic region and adjacent leg portions of a person and accommodating expansion of the device.

12. A hygiene device in the nature of a short according to claim 11, and an absorptive pad borne by the cloth so as to be disposed below the pelvic region and between the legs of the person.

13. A hygiene device in the nature of a short according to claim 11, wherein the cloth is layers of absorbent cotton blend material and a thin plastic backing.

14. A hygiene device in the nature of a short according to claim 11, and an elastic element associated with the bottom of each leg of the short for sealingly engaging the corresponding leg of a person.

15. A hygiene device in the nature of a short according to claim 12, wherein the cloth is layers of absorbent cotton blend material and a thin plastic backing.

16. A hygiene device in the nature of a short according to claim 14, and an elastic element associated with the upper end of the short for helping support the device on a person.

17. A device in the nature of a short, comprising a cloth having a main body portion having separated front and back halves with side edges for encircling the pelvic region and two leg portions for encircling adjacent leg portions of a person, and a wide vertical elastic side band attached to the side edges of the cloth front and back halves for holding the cloth portions snug about the person's pelvic region and leg portions and accommodating expansion of the device.

18. A device in the nature of a short according to claim 17, wherein there is a vertical elastic side band on each side of the short for holding the cloth portions snug about the person's pelvic region and leg portions.

19. A device in the nature of a short according to claim 18, and an elastic band associated with the bottom of each leg of the short for sealingly engaging the corresponding leg of a person.

20. A device in the nature of a short according to claim 19, and an elastic element associated with the upper end of the short for helping support the device on the person.

\* \* \* \* \*